United States Patent [19]

Ciecwisz et al.

[11] Patent Number: 5,440,295
[45] Date of Patent: Aug. 8, 1995

[54] APPARATUS AND METHOD FOR PREVENTING UNAUTHORIZED REMOVAL OF A NEWBORN INFANT FROM A PREDETERMINED AREA

[76] Inventors: Richard A. Ciecwisz, 482 Cobain Rd., Jackson, N.J. 08527; John Cardello, 1615 Beverly Rd., Forked River, N.J. 08731

[21] Appl. No.: 236,316
[22] Filed: May 2, 1994
[51] Int. Cl.$^6$ .............................. G08B 23/00
[52] U.S. Cl. .................... 340/573; 340/551; 340/571; 340/572; 606/120
[58] Field of Search ............... 340/573, 539, 551, 571, 340/572; 606/120

[56] References Cited

U.S. PATENT DOCUMENTS

| | | |
|---|---|---|
| 3,016,056 | 1/1962 | Jacobs . |
| 3,204,636 | 9/1965 | Kariher et al. . |
| 3,247,852 | 4/1966 | Schneider . |
| 3,292,080 | 12/1966 | Trikilis . |
| 3,383,797 | 5/1968 | Trikilis . |
| 3,418,613 | 12/1968 | Trikilis . |
| 3,524,225 | 8/1970 | Trikilis . |
| 4,212,303 | 7/1980 | Nolan . |
| 4,694,284 | 9/1987 | LeVeille et al. . |
| 4,899,134 | 2/1990 | Wheeless, Jr. . |
| 4,973,944 | 11/1990 | Mapletta . |
| 5,006,830 | 4/1991 | Merritt . |
| 5,032,823 | 7/1991 | Bower et al. . |
| 5,047,750 | 9/1991 | Hector . |

Primary Examiner—Brent Swarthout
Assistant Examiner—Albert K. Wong
Attorney, Agent, or Firm—Sperry, Zoda & Kane

[57] ABSTRACT

An apparatus usable for controlling the removal of newborn infants from a maternity ward or other restricted area which includes an electrical transponder member detachably securable to an umbilical cord clamping device such that the transponder is attached to the umbilical cord clamping device when clamped upon the umbilical cord of a newborn infant. The transponder members are positioned within a housing and include a stud extending outwardly therefrom which is adapted to extend through a securement opening defined by the umbilical cord clamping device. When the umbilical cord clamping device is closed the securement opening closes somewhat and thereby attaches the transponder unit with respect to the umbilical cord of the infant. When the infant is discharged from the maternity ward the transponder units can be recycled by removal thereof simultaneously with the umbilical cord clamp.

25 Claims, 4 Drawing Sheets

APPARATUS AND METHOD FOR PREVENTING UNAUTHORIZED REMOVAL OF A NEWBORN INFANT FROM A PREDETERMINED AREA

BACKGROUND OF THE INVENTION

1. Field of the Invention

The present invention deals with the field of devices for controlling exiting from a predefined area. In particular the present invention is usable for restricting the removal of infants from predetermined areas such as the maternity ward of a hospital other than by fully authorized removal by specifically authorized personnel such as the parent of the child or specific health care workers.

Personal security of infants within the maternity wards of hospitals or other similar areas has become a very dangerous problem for which hospitals are required to take appropriate security measures. Many different types of alarm or emergency systems have been devised to prevent kidnapping of infants from maternity wards. The present invention provides a novel advance in the apparatus and method for preventing such unauthorized removal of infants.

2. Description of the Prior Art

Many methods and apparatus have been devised for controlling and restricting the removal of newborn infants from maternity wards or other similar areas such as shown in U.S. Pat. No. 3,016,056 patented Jan. 9, 1962 to J. B. Jacobs on a "Method Of Identifying Newly Born Infants"; and U.S. Pat. No. 3,204,636 patented Sep. 7, 1965 to D. H. Kariher et al on a "Funis Clamp"; and U.S. Pat. No. 3,247,852 patented Apr. 26, 1966 to J. D. Schneider and assigned to Hollister Incorporated on an "Umbilical Cord Clamp"; and U.S. Pat. No. 3,292,080 patented Dec. 13, 1966 to E. M. Trikilis on a "System And Method For Preventing Pilferage By Detection Of Magnetic Fields"; and U.S. Pat. No. 3,383,797 patented May 21, 1968 to E. M. Trikilis on a "Turnstile"; and U.S. Pat. No. 3,418,613 patented Dec. 24, 1968 to E. M. Trikilis on a "Method Of Magnetizing A Large Quantity of Bulk Articles"; and U.S. Pat. No. 3,524,225 patented Aug. 18, 1970 to E. M. Trikilis on a "Locking Assembly"; and U.S. Pat. No. 4,212,303 patented Jul. 15, 1980 to J. Noland and assigned to Hollister Incorporated on an "Umbilical Cord Clamp"; and U.S. Pat. No. 4,694,284 patented Sep. 15, 1987 to S. Leveille et al on an "Abduction-Preventing Collar"; and U.S. Pat. No. 4,899,134 patented Feb. 6, 1990 to C. Wheeless, Jr. on a "Newborn Anti-Theft Device"; and U.S. Pat. No. 4,973,944 patented Nov. 27, 1990 to G. Maletta on an "Electrical Signal And Alarm Protection Proximity Device"; and U.S. Pat. No. 5,006,830 patented Apr. 9, 1991 to R. Merritt on a "Method And Device For Deterring The Unauthorized Removal Of A Newborn From A Defined Area"; and U.S. Pat. No. 5,032,823 patented Jul. 16, 1991 to D. Bower et al and assigned to Digital Products Corporation on a "Secure Personnel Monitoring System" and U.S. Pat. No. 5,047,750 patented Sep. 10, 1991 to L. Hector on a "Non-Intrusive Infant Security System".

SUMMARY OF THE INVENTION

The present invention provides a novel apparatus which can be used for controlling and specifically preventing unauthorized removal of newborn infants from maternity wards or other predetermined areas. The apparatus may include an umbilical cord clamping device including an interconnecting member of flexibly resilient material which may include a first and second attachment end which are each movable with respect to one another between a closed and open position. This interconnecting member is preferably adapted to retain a first attachment end and a second attachment end normally in the opened position spatially separated from one another. Movement from this open position to the closed position can be achieved to facilitate attachment of the umbilical cord clamp with respect to the umbilical cord of a newborn infant. Preferably this interconnecting member also defines a securement opening therein for securement of a transponder or other member thereto.

The umbilical cord clamping device includes a first arm fixedly secured to the first attachment end of the interconnecting member and this first arm preferably includes a first clamping section extending therealong preferably with teeth to facilitate engagement. In a similar manner a second arm is fixedly secured to the second attachment end of the second interconnecting member. This second arm also preferably includes a second clamping section thereon which may include teeth to facilitate clamping.

A first engagement device is positioned on the first arm with the first clamping section located between the first attachment end and the first engagement device. This first engagement device preferably includes a prong receiving recess and two prong engaging shoulders therein. A second engagement device may be positioned on the second arm with the second clamping section located between the second attachment end and the second engagement device. This second engagement device of the second arm preferably includes two oppositely flexible prong members which are adapted to extend into the prong receiving recess for detachable securement therein. The second engagement device is selectively engageable with respect to the first engagement device on the first arm to selectively retain the first arm and the second arm in a closed position with the first clamping section and the second clamping section in a closed position adjacent to one another clamping upon an umbilical cord of an infant positioned therebetween.

A first gripping pad is preferably defined on the first arm to facilitate closing of the umbilical cord clamping device upon an umbilical cord positioned between the two clamping sections. A second gripping means is positioned on the second arm means also to facilitate closing of the umbilical cord clamping device upon an infant umbilical cord positioned between the first and second clamping sections.

A transponder member is preferably detachably securable to the interconnecting member of the umbilical cord. This transponder member preferably includes a transponder housing which is waterproof to prevent water damage therein and which includes a transponder stud member integral with respect to the transponder housing and extending outwardly therefrom. An electronic transponder unit is preferably positioned within the transponder housing and may include an active electronic signal generating device and a battery for powering thereof or can include a passive electric transponder signal unit.

Preferably the transponder stud member of the transponder housing is detachably engageable extending through the securement opening defined in the interconnecting member to selectively attach the transponder member and the electronic transponder unit with respect to an umbilical cord clamping device responsive to being in the closed position retaining an umbilical cord therewith. This transponder stud member may also include a lip extending circumferentially around the upper end thereof in order to facilitate the detachable retainment of the stud member with the securement opening when the umbilical cord clamping device is in the closed position.

The apparatus of the present invention may further include an electronic sensing device positioned in at least one location adjacent the predetermined area which is capable of detecting an attempted removal of an electronic transponder unit from within the predetermined area. The apparatus may also include an alarm device in electrical communication with respect to the electronic sensing device which is responsive to the detection of an attempted removal of an electronic transponder unit from within the predetermined area to generate an alarm signal. In the more complete systems a selective deactivation device will be in electrical communication with respect to the electronic sensing device and is responsive to authorize operation thereof to deactivate operation of the electronic sensing means. In the most complete systems an exit control device will be responsive to actuation of the electronic sensing means to positively restrict exiting from a predetermined area. Such exit control devices can inhibit movement of doorways, can initiate the activation of exit barriers or could, for example, cause cessation of operation of an elevator. All of these exit control devices would be responsive to sensing of an attempted removal of a transponder to eliminate all access to exits from the predetermined area until the alarm condition can be analyzed.

In operation the apparatus of the present invention can comprise a method which will provide an electronic sensing device positioned in at least one location adjacent to a predetermined area to detect an attempt to remove a transponder member from within the predetermined area. Furthermore an alarm device can be provided in electrical communication with respect to the electronic sensing device which is responsive to detection of an attempt to remove a transponder member from a predetermined area to generate an alarm signal. Furthermore, in accordance with the method of the present invention, a transponder member will be detachably securable with respect to the umbilical cord clamp of a newborn infant. Thereafter the umbilical cord clamp will be clamped onto the umbilical cord of a newborn infant with this transponder member detachably secured thereto. At a later date when the infant is released from the maternity ward or other predetermined area the umbilical cord clamp and the transponder member can both be removed from the umbilical cord of the infant. The transponder member can then be detached from the umbilical cord clamp and can be collected in a predetermined reservoir to be made available again for re-usage in accordance with the method of the present invention. Transponder members can be refurbished by cleaning and testing thereof. They can also be disinfected as needed.

It is an object of the present invention to provide an apparatus and method for preventing unauthorized removal of a newborn infant from a predetermined area wherein security of maternity wards can be achieved at minimal initial capital costs.

It is an object of the present invention to provide an apparatus and method for preventing unauthorized removal of a newborn infant from a predetermined area wherein security of maternity wards in hospitals can be achieved with minimal maintenance requirements.

It is an object of the present invention to provide an apparatus and method for preventing unauthorized removal of a newborn infant from a predetermined area wherein an efficient security system can be provided for maternity wards at hospitals.

It is an object of the present invention to provide an apparatus and method for preventing unauthorized removal of a newborn infant from a predetermined area wherein switching of children at birth within the maternity wards of hospitals can be prevented.

It is an object of the present invention to provide an apparatus and method for preventing unauthorized removal of a newborn infant from a predetermined area wherein infant abduction from maternity wards of hospitals can be easily and efficiently controlled.

It is an object of the present invention to provide an apparatus and method for preventing unauthorized removal of a newborn infant from a predetermined area wherein an electronic transponder unit is hidden from a potential abductor.

It is an object of the present invention to provide an apparatus and method for preventing unauthorized removal of a newborn infant from a predetermined area wherein use with an active or passive transponder is possible.

It is an object of the present invention to provide an apparatus and method for preventing unauthorized removal of a newborn infant from a predetermined area wherein recycling of used transponders is possible.

It is an object of the present invention to provide an apparatus and method for preventing unauthorized removal of a newborn infant from a predetermined area wherein a transponder is detachably secured with an infant simultaneously with securing to the umbilical cord of a newborn infant.

It is an object of the present invention to provide an apparatus and method for preventing unauthorized removal of a newborn infant from a predetermined area wherein a decoy wristband can be provided for newborn infants to enhance protection thereof.

It is an object of the present invention to provide an apparatus and method for preventing unauthorized removal of a newborn infant from a predetermined area wherein exits from the maternity ward or other predetermined area can be closed responsive to an attempted removal of a transponder from the allowed area.

It is an object of the present invention to provide an apparatus and method for preventing unauthorized removal of a newborn infant from a predetermined area wherein an alarm can be provided for alerting security personnel to an attempted unauthorized removal of an infant from a maternity ward.

It is an object of the present invention to provide an apparatus and method for preventing unauthorized removal of a newborn infant from a predetermined area wherein selective deactivation by authorized operators such as being key controlled can be used to allow movement of an infant by authorized health care personnel or by a parent from the maternity ward for X-rays or other fully authorized removal.

It is an object of the present invention to provide an apparatus and method for preventing unauthorized removal of a newborn infant from a predetermined area wherein a battery means is utilized for powering of the active electronic signal generating device of the transponder.

It is an object of the present invention to provide an apparatus and method for preventing unauthorized removal of a newborn infant from a predetermined area wherein a battery powers an active transponder unit wherein the battery life is at least two to four years.

It is an object of the present invention to provide an apparatus and method for preventing unauthorized removal of a newborn infant from a predetermined area wherein both accidental and intentional switching or abduction can be prevented.

It is an object of the present invention to provide an apparatus and method for preventing unauthorized removal of a newborn infant from a predetermined area wherein no additional clamps or external equipment need be attached to a newborn infant other than the umbilical cord clamp which is used in the conventional manner.

It is an object of the present invention to provide an apparatus and method for preventing unauthorized removal of a newborn infant from a predetermined area wherein a transponder can be attached to an infant utilizing a conventional design of an umbilical cord.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

DETAILED DESCRIPTION OF THE PREFERRED EMBODIMENT

Figure 1:
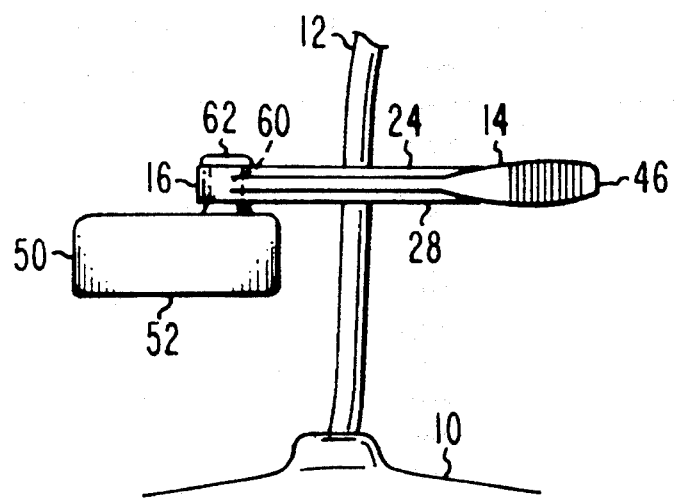
FIG. 1 is a front plan view of an embodiment of the apparatus of the present invention showing the umbilical cord clamping means in position clamped upon the umbilical cord of an infant with the transponder housing detachably secured thereto.

The present invention provides an apparatus and method for preventing unauthorized removal of an newborn infant 10 from a predetermined area such as a maternity ward or the like. The design includes the use of an umbilical cord clamp 14 adapted to be attached to the umbilical cord 12 of a newborn infant 10 immediately after birth.

The construction of the umbilical cord clamp 14 includes an interconnecting member 16 having a first attachment end 18 and a second attachment end 20 which are spatially disposed with respect to one another and are movable with respect to one another. Preferably the interconnecting member 16 is formed of a flexible material to facilitate movement of the first attachment end 18 and the second attachment end 20 with respect to one another between an open position 22 and a closed position 24.

Preferably the interconnecting member 16 defines a securement opening 26 therein to facilitate securement of a transponder housing thereto.

The umbilical cord clamp 14 includes a first arm 28 which is secured with respect to the first attachment end 18 of the interconnecting member 16. In a similar manner a second arm 32 is secured to the second attachment end 20 to be movable therewith. The second arm 32 defines a second clamping section 34 extending therealong. In a similar manner the first arm 28 includes a first clamping section 30 therealong. Both clamping sections 30 and 34 preferably are formed with teeth therein to facilitate engagement of an umbilical cord 12 positioned therebetween.

The first arm 28 also includes a first engagement device 36 thereon which preferably includes a prong receiving recess 38 and a prong engaging shoulder 39. A second engagement device 40 is positioned on the second arm 32 and includes preferably a prong member 42 which may comprise a single or dual prong member with each prong member having a prong tab 44. The first engagement device 36 and second engagement device 40 are positionable adjacent one another such as to engage one another such as with the prong member 42 extending into the prong receiving recess 38 and the prong tab or tabs 44 extending over the engagement shoulder or shoulders 39. With this construction the and the engagement of the first engagement device 36 with respect to the second engagement device 40 an umbilical cord 12 can be easily clamped therebetween to facilitate closing of the umbilical cord and to aid in identification as described herebelow.

To facilitate closing movement of the first arm 28 and second arm 32 to the closed position with the first clamping second 30 and the second clamping section 34 positioned adjacent to one another while clamping an umbilical cord 12, a first gripping pad 46 may be defined on the first arm 28 immediately adjacent the first engagement device 36. In a similar manner a second gripping pad 48 may be positioned on the second arm 32 in a position immediately adjacent to the second engagement device 40. Engagement of these two gripping pads by the thumb and forefinger of a health care worker can greatly facilitate the engaging of the first and second engagement devices 36 and 40 with respect to one another to facilitate closing of the umbilical cord clamp 14 upon an umbilical cord 12.

The present invention also provides a transponder member 50 which includes a transponder housing 52 adapted to retain therein an electronic transponder unit 54. This electronic transponder unit 54 can comprise an active electronic signal generating device 56 thereby requiring a power source such as a battery 58 which could be a lithium battery. On the other hand the electronic transponder unit 54 could be a passive transponder circuit. With either the active or the passive configurations of the electronic transponder unit 54 interaction with respect to a sensing means can be achieved in accordance with operation of the present invention.

The transponder housing 52 preferably includes a transponder stud member 60 on the external surface thereof with a transponder stud lip 62 at the outermost end thereof. This transponder stud member 60 is adapted to extend into the securement opening 26 of the umbilical cord clamp 14 of the present invention and is adapted to be attached thereto responsive to closing of the umbilical cord clamp 14 upon an umbilical cord 12. This closing will reduce the inside diameter of the securement opening 26 thereby allowing it to detachably retain the transponder stud member 60 and as well the entire transponder member 50 therein.

With the configuration described hereabove a health care worker can easily attach the transponder member 50 to an umbilical cord clamp 14 in the open position 22. Then the user can take the umbilical cord clamp 14 and close it upon the umbilical cord 12 of an infant 10 and in this manner simultaneously apply the umbilical cord clamp as conventionally done immediately after birth of the baby while at the same time secure the transponder member 50 with respect to the infant by being secured with respect to the umbilical cord clamp 14 itself and in this manner provide a means for identification and movement control of the infant during the time the infant is within the maternity ward or other predetermined area.

Figure 7:
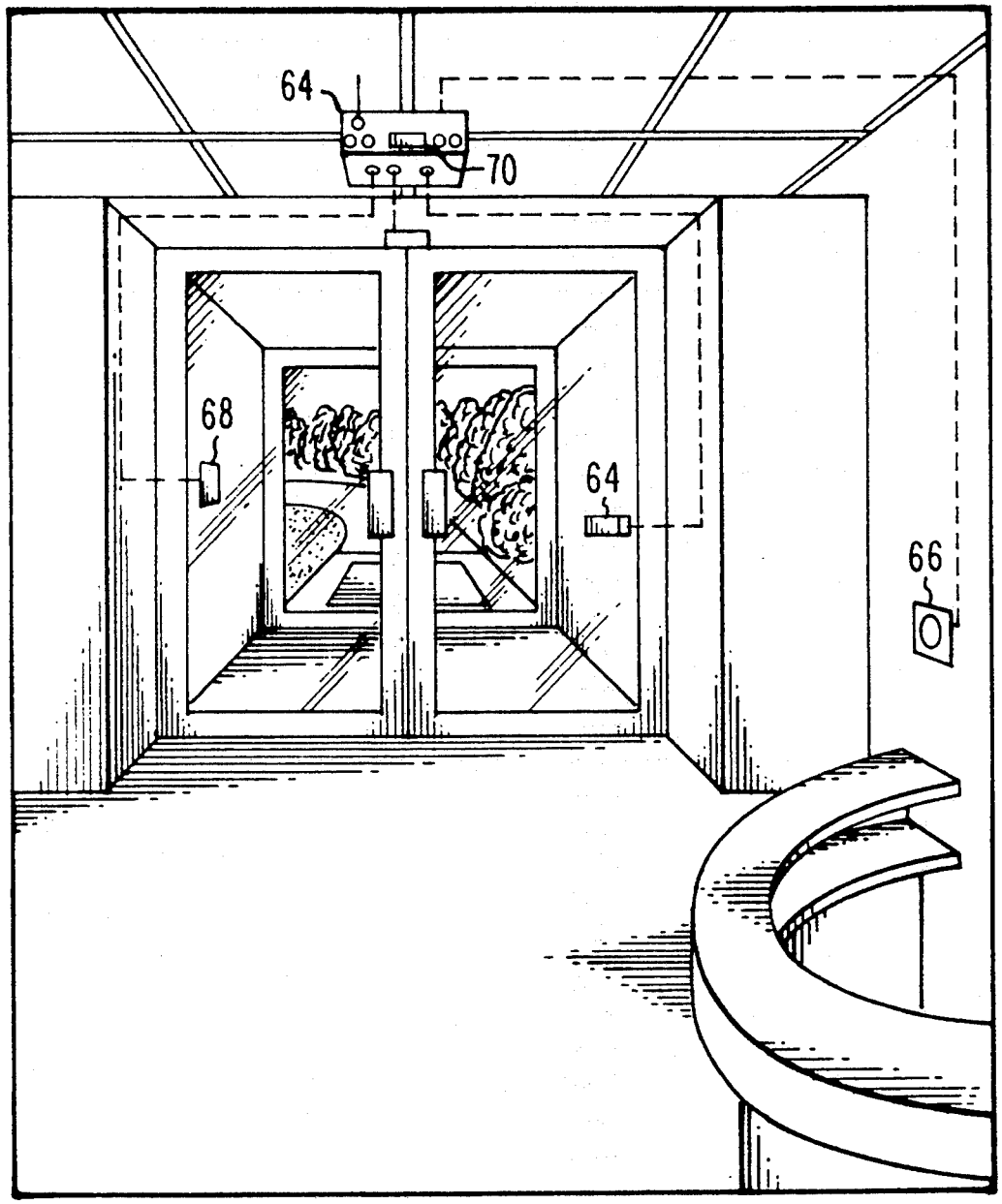
FIG. 7 is an illustration of positioning of an embodiment of the elements of the present invention shown controlling an exit from the predetermined area.

The apparatus of the present invention further includes an electronic sensing means 64 which is adapted to sense the movement of an electronic transponder unit 54 within the transponder member 50 thereby. These electronic sensing means 64 can be positioned at any exit locations from the predetermined area such as doorways, archways, elevators, stairwells, hallways or the like. In this manner whenever an infant 10 with the umbilical cord clamp 14 and the transponder member 50 secured thereto passes the electronic sensing means 64 the sensing means itself will be activated. Preferably the electronic sensing means 64 is connected to an alarm means 66 to generate some type of audio, visual or silent alarm to notify security or other authorized personnel, such as hospital security in a maternity ward, that an unauthorized attempt at removal of an infant is occurring. This control can further include an exit control means 70 which as shown in FIG. 7 can be used to lock a door to prevent unauthorized exiting of an infant therethrough. The exit control means 70 can also be used to render an elevator in operative or to activate a gate or other means for preventing the actual exiting of the intruder with the infant 10.

There are certainly situations wherein it will be necessary to move an infant to various locations by authorized health care workers or by the parents of the infant. An example might be to move the infant from the maternity ward to another location in the hospital to have an X-ray taken. For this purpose a selective deactivation means 68 can be included which could be key operated or electronically or otherwise operated in such a manner as to deactivate the electronic sensing means 64 responsive to activation of the selective deactivation means 68 by a nurse, parent or other health care worker prior to movement to, for example, the X-ray location.

Figure 3:
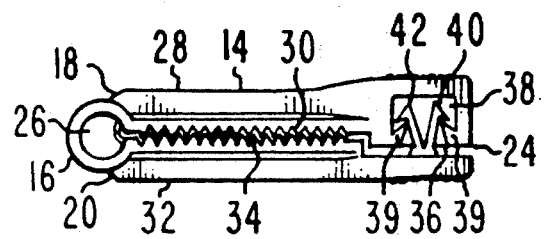
FIG. 3 is a plan view of an embodiment of the umbilical cord clamping device of the present invention shown in the closed position.
Figure 4:
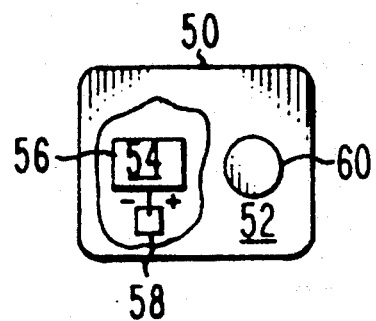
FIG. 4 is a top plan view of an embodiment of a transponder member of the present invention.
Figure 5:
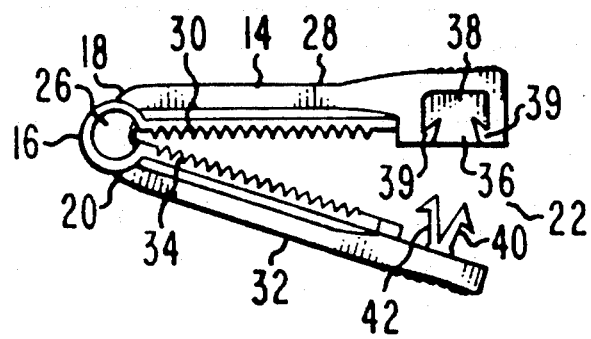
FIG. 5 is a plan view of an embodiment of an umbilical cord clamping device of the present invention shown in the open position.
Figure 6:
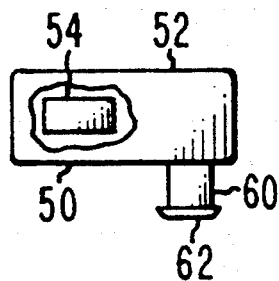
FIG. 6 is a side plan view of an embodiment of the transponder member of the present invention.

In the preferred configuration of transponder member 50 as shown in FIGS. 4 and 6 the housing will include an integral stud extending outwardly therefrom and being generally cylindrically shaped. This stud 60 will include a lip 62 at the outermost extremity thereof thereby facilitating interlocking of the stud and the electronic transponder unit 54 attached thereto with respect to the umbilical cord clamp 14. This stud 60 can extend through the opening in the umbilical cord clamp 14 as shown best in FIGS. 1 and 3 in such a manner as to be detachably retained therein when the umbilical cord clamp 14 is in the closed position. Upon release of the infant from the hospital the umbilical cord clamp 14 can be released thereby allowing for the transponder to be placed in a collection bin for recycling or refurbishing thereof. Such refurbishing can include disinfecting and/or sterilizing of the transponder prior to next usage thereof.

Figure 2:
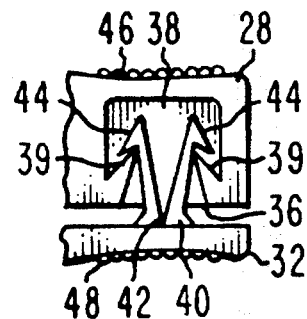
FIG. 2 is an exploded view of the first and second engagement means shown secured with respect to one another of the umbilical cord clamping device.

The configuration of the first engagement device 36 and the second engagement device 40 can be of any conventional engagement configuration. However, the preferred configuration is shown in the exploded view shown as FIG. 2. There we see two oppositely disposed flexible prong members 42 each having a prong tab 44 extending outwardly therefrom into engagement with respect to a shoulder 39. In the configuration shown in FIG. 2 two prong tabs 44 positioned on two oppositely disposed prong members 42 will engage two oppositely positioned shoulders within the prong receiving recess 38. With this configuration secure engagement between the first and second engagement devices 36 and 40 will be achievable.

The operation of the electronic sensing means 64 can be adapted to sense an electric signal generated by the electronic transponder unit 54 if that unit is an active electronic signal generating device 56. Such a device 56 can utilize a battery 58 such as a lithium battery. Alternatively the electronic transponder unit 54 can comprise a passive electronic circuit means which is adapted to interact with respect to a signal generated from the electronic sensing means 64 to indicate the presence of the transponder unit within the security defined area. Either of these two configurations will effectively work in a similar manner in regard to the generation of alarm signals through the alarm means 66.

One of the novel aspects of the present invention is that the closing of the umbilical cord clamp 14 upon the umbilical cord 12 of the infant 10 will simultaneously also achieve attachment of the transponder member 50 with respect to the infant 10. Thus the umbilical cord clamp will comprise the dual purpose of acting as a standard umbilical cord clamp 14 while at the same time providing the means of securement of the transponder member 50 with respect to the infant 10.

Figure 8:
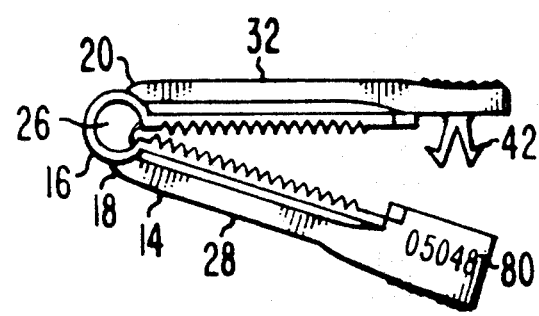
FIG. 8 is a side plan view of an embodiment of the transponder member of the present invention showing the positioning of an identification number on an embodiment of the umbilical clamp.

The security kit sold with the present invention may include additional items such as dummy wristbands, authorized user wristbands or may include identification numbers directly placed on the umbilical cord clamp itself such as indicia 90 shown on FIG. 8. The use of any of these devices are added options which aids in the security of the overall system. It is also preferable that the transponder housing 52 be waterproof in order avoid electrical breakdown problems commonly associated with high moisture environments to which the transponder housing of the present invention may be exposed regularly.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

I claim:

1. An apparatus for preventing unauthorized removal of a newborn infant from a predetermined area comprising:
   A. an umbilical cord clamping means comprising:
      (1) an interconnecting member having a first attachment end and a second attachment end movable with respect to one another, said interconnecting member adapted to retain said first attachment end and said second attachment end in steady state in an open position spatially separated from each other, said interconnecting member defining a securement opening extending therethrough;
      (2) a first arm means fixedly secured to said first attachment end of said interconnecting member, said first arm means including a first clamping section thereon;
      (3) a second arm means fixedly secured to said second attachment end of said interconnecting member, said second arm means including a second clamping section thereon;
      (4) a first engagement means on said first arm means;
      (5) a second engagement means on said second arm means and being selectively engageable with respect to said first engagement means on said first engagement means to retain said first arm means and said second arm means in a closed position with said first clamping section and said second clamping section in a closed position adjacent to one another clamping an umbilical cord therebetween;
   B. a transponder member being detachably secured to said interconnecting member of said umbilical cord clamping means, said transponder member comprising;
      (1) a transponder housing means;
      (2) an electronic transponder unit positioned within said transponder housing means;
      (3) a transponder attachment means attached to said transponder housing means and extending outwardly therefrom, said transponder attachment means being detachably engageable with respect to said interconnecting member to selectively attach said transponder member and said electronic transponder unit with respect to said umbilical cord clamping means responsive to being in a closed position retaining an umbilical cord therewith, said transponder attachment means including a transponder stud member adapted to extend through said securement opening defined in said interconnecting member to facilitate securement of said transponder member with respect to said umbilical cord clamping means; and
   C. an electronic sensing means positioned in at least one location adjacent the predetermined area and being capable of detecting the attempted removal of said electronic transponder unit from within the predetermined area.

2. An apparatus for preventing unauthorized removal of a newborn infant from a predetermined area as defined in claim 1 wherein said transponder stud member includes a lip means located thereon to facilitate detachable securement thereof with respect to said securement opening defined in the interconnecting member.

3. An apparatus for preventing unauthorized removal of a newborn infant from a predetermined area as defined in claim 1 further comprising an alarm means in electrical communication with respect to said electronic sensing means and being responsive to detection of an attempted removal of said electronic transponder unit from within the predetermined area to generate an alarm signal.

4. An apparatus for preventing unauthorized removal of a newborn infant from a predetermined area as defined in claim 1 wherein said electronic transponder unit is a passive electronic circuit means.

5. An apparatus for preventing unauthorized removal of a newborn infant from a predetermined area as defined in claim 1 wherein said electronic transponder unit is an active electronic signal generating means.

6. An apparatus for preventing unauthorized removal of a newborn infant from a predetermined area as defined in claim 5 wherein said transponder member further includes a battery means therein to power active generation of an electrical signal.

7. An apparatus for preventing unauthorized removal of a newborn infant from a predetermined area as defined in claim 6 wherein said battery means comprises a lithium battery.

8. An apparatus for preventing unauthorized removal of a newborn infant from a predetermined area as defined in claim 1 wherein said second engagement means comprises two flexible prong members and wherein said first engagement means comprising a prong receiving recess means adapted to detachably engage said two flexible prong members for selective attachment between said first arms means and said second arm means.

9. An apparatus for preventing unauthorized removal of a newborn infant from a predetermined area as defined in claim 1 wherein said first clamping section is positioned on said first arm means between said first engagement means thereof and said first attachment end.

10. An apparatus for preventing unauthorized removal of a newborn infant from a predetermined area as defined in claim 1 wherein said second clamping section is positioned on said second arm means between said second engagement means thereof and said second attachment end.

11. An apparatus for preventing unauthorized removal of a newborn infant from a predetermined area as defined in claim 1 wherein said transponder housing means is waterproof to prevent water damage to said electronic transponder unit.

12. An apparatus for preventing unauthorized removal of a newborn infant from a predetermined area as defined in claim 1 further comprising a first gripping means on said first arm means and a second gripping means on said second arm means to facilitate closing of said umbilical cord clamping means upon an umbilical cord positioned therebetween.

13. An apparatus for preventing unauthorized removal of a newborn infant from a predetermined area as defined in claim 1 further comprising a selective deactivation means being in electrical communication with respect to said electronic sensing means and being responsive to authorized operation thereof to selectively deactivate operation of said electronic sensing means.

14. An apparatus for preventing unauthorized removal of a newborn infant from a predetermined area as defined in claim 1 further comprising an exit control means being responsive to activation of said electronic sensing means to restrict exiting from the predetermined area.

15. An apparatus for preventing unauthorized removal of a newborn infant from a predetermined area as defined in claim 1 wherein said interconnecting member is flexibly resilient to facilitate movement of said first attachment end and said second attachment end with respect to one another.

16. An apparatus for preventing unauthorized removal of a newborn infant from a predetermined area as defined in claim 1 wherein said transponder stud member is integral with respect to said transponder housing means.

17. An apparatus for preventing unauthorized removal of a newborn infant from a predetermined area comprising:
   A. an umbilical cord clamping means comprising:
   (1) an interconnecting member of flexibly resilient material having a first attachment end and a second attachment end movable with respect to one another, said interconnecting member adapted to retain said first attachment end and said second attachment end in steady state in an open position spatially separated from each other, said interconnecting member defining a securement opening therein;
   (2) a first arm means fixedly secured to said first attachment end of said interconnecting member, said first arm means including a first clamping section thereon;
   (3) a second arm means fixedly secured to said second attachment end of said interconnecting member, said second arm means including a second clamping section thereon;
   (4) a first engagement means positioned on said first arm means with said first clamping section located between said first attachment end and said first engagement means, said first engagement means comprising a prong receiving recess means;
   (5) a second engagement means positioned on said second arm means with said second clamping section located between said second attachment end and said second engagement means, said second engagement means of said second arm means comprising two flexible prong members being adapted to extend into said prong receiving recess for detachable securement therein, said second engagement means being selectively engageable with respect to said first engagement means on said first arm means to selectively retain said first arm means and said second arm means in a closed position with said first clamping section and said second clamping section in a closed position adjacent to one another clamping an umbilical cord therebetween;
   (6) a first gripping means on said first arm means to facilitate closing of said umbilical cord clamping means upon an umbilical cord positioned between said first clamping section and said second clamping section;
   (7) a second gripping means on said second arm means to facilitate closing of said umbilical cord clamping means upon an umbilical cord positioned between said first clamping section and said second clamping section;

B. a transponder member being detachably securable to said interconnecting member of said umbilical cord clamping means, said transponder member comprising;
   (1) a transponder housing means being waterproof to prevent water damage therein;
   (2) an electronic transponder unit positioned within said transponder housing means, said electronic transponder unit including an active electronic signal generating means and a battery means for powering thereof;
   (3) a transponder stud member integral with respect to said transponder housing means and extending outwardly therefrom, said transponder stud member being detachably engageable extending through said securement opening defined in said interconnecting member to selectively attach said transponder member and said electronic transponder unit with respect to said umbilical cord clamping means responsive to being in a closed position retaining an umbilical cord therewith, said transponder stud member including a lip means extending therearound to facilitate detachable retaining of said stud member within said securement opening;

C. an electronic sensing means positioned in at least one location adjacent the predetermined area and being capable of detecting an attempted removal of said electronic transponder unit from within the predetermined area;
   D. an alarm means in electrical communication with respect to said electronic sensing means and being responsive to detection of an attempted removal of said electronic transponder unit from within the predetermined area to generate an alarm signal;
   E. a selective deactivation means being in electrical communication with respect to said electronic sensing means and being responsive to authorized operation thereof to deactivate operation of said electronic sensing means; and
   F. an exit control means being responsive to activation of said electronic sensing means to restrict exiting from the predetermined area.

18. A method for preventing unauthorized removal of a newborn infant from a predetermined area comprising:
   A. providing of an electronic sensing device positioned in at least one location adjacent to the predetermined area to detect a attempt to remove a transponder member from within the predetermined area;
   B. providing of an alarm device in electrical communication with respect to the electronic sensing device and being responsive to detection of an attempt to remove a transponder member from the predetermined area to generate an alarm signal;
   C. clamping of the umbilical cord clamp onto the umbilical cord of a newborn infant with the transponder member detachably secured thereto and simultaneously securing of a transponder member detachably with respect to an umbilical cord clamp for a newborn infant;
   D. removal of the umbilical cord clamp and transponder member attached thereto upon release of an infant from the predetermined area;
   E. detaching of the transponder member from the umbilical cord clamp; and F. collecting of the transponder members to be made available for use again for said securing of a transponder member detachably with respect to an umbilical cord clamp for a newborn infant.

19. A method for preventing unauthorized removal of a newborn infant from a predetermined area as defined in claim 18 further comprising refurbishing of the transponder members after said collecting thereof to facilitate cleanliness of usage and efficiency of operation thereof.

20. A method for preventing unauthorized removal of a newborn infant from a predetermined area as defined in claim 19 wherein said refurbishing includes disinfecting of the transponder members.

21. A method for preventing unauthorized removal of a newborn infant from a predetermined area as defined in claim 19 wherein said refurbishing includes sterilizing of the transponder members.

22. A method for preventing unauthorized removal of a newborn infant from a predetermined area as defined in claim 18 wherein said refurbishing includes checking of the electronic operation of the transponder members.

23. A method for preventing unauthorized removal of a newborn infant from a predetermined area as defined in claim 18 further comprising marking of said umbilical cord clamp with indicia directly thereon to facilitate identification of an infant with the clamp attached.

24. A method for preventing unauthorized removal of a newborn infant from a predetermined area as defined in claim 18 further including controlling of exiting availability from the predetermined area responsive to detection of an attempted removal of a transponder member therefrom.

25. A method for preventing unauthorized removal of a newborn infant from a predetermined area as defined in claim 18 further comprising selective deactivating of the alarm device to allow authorized removal of an infant from the predetermined area as desired.

* * * * *